United States Patent

Czura et al.

[11] Patent Number: 5,562,715
[45] Date of Patent: Oct. 8, 1996

[54] CARDIAC PULSE GENERATOR

[76] Inventors: John J. Czura, 5030 Columbia Rd., Grovetown, Ga. 30813; Randolph H. Kricke, 4128 Heritage Ridge, Evans, Ga. 30809

[21] Appl. No.: 353,221

[22] Filed: Dec. 1, 1994

[51] Int. Cl.$^6$ ............................................. A61N 1/375
[52] U.S. Cl. ............................................................. 607/36
[58] Field of Search ............................... 607/9, 36, 2, 4, 607/5

[56] References Cited

U.S. PATENT DOCUMENTS

| | | |
|---|---|---|
| 3,735,766 | 5/1973 | Bowers et al. |
| 3,866,616 | 2/1975 | Purdy et al. ............................ 607/36 |
| 3,918,460 | 11/1975 | King et al. |
| 3,924,640 | 12/1975 | King. |
| 3,943,937 | 3/1976 | King et al. |
| 3,971,388 | 7/1976 | Cowdery. |
| 4,010,759 | 3/1977 | Boer. |
| 4,369,791 | 1/1983 | Friedman ............................... 607/36 |
| 5,220,929 | 6/1993 | Marquit. |
| 5,282,841 | 2/1994 | Szvzkowski. |
| 5,385,574 | 1/1995 | Hauser et al. ............................. 607/9 |

*Primary Examiner*—William E. Kamm
*Attorney, Agent, or Firm*—Dickinson, Wright, Moon, Van Dusen & Freeman

[57] ABSTRACT

A pacemaker may be implanted with equal facility on either side of a patient's chest without causing torque in the lead wires and avoiding unwanted local muscle stimulation. In one embodiment, the casing of the pacemaker is provided on opposite sides with a removable tab that covers an indifferent electrode so that when the device is implanted the appropriate tab may be removed to expose the electrode facing the patient's chest cavity. In a second embodiment, a portion along the edge of the pacemaker is left exposed to serve as the indifferent electrode, again allowing the device to be implanted with equal facility on either side of the chest without torque in the lead wires. Furthermore, since the edge of the device is not facing toward the patient's pectoral muscles, the device avoids unwanted pectoral twitching.

12 Claims, 1 Drawing Sheet

CARDIAC PULSE GENERATOR

TECHNICAL FIELD

This invention relates generally to the art of pacemakers, and in particular to the coatings on pacemakers.

BACKGROUND

Various pacemakers are known to the prior art. Typically, these devices consist of a metal casing which houses a pulse generator. A terminal connector, which is in electrical contact with the pulse generator, extends from the casing and provides an interface from which one or more lead wires extend. The ends of these lead wires are connected by tines or helical screws to the tissue to be stimulated (i.e., the epicardial tissue). The casing of the pacemaker is usually coated with a physiologically acceptable resin which insulates the casing both chemically and electrically, from the surrounding tissues.

Pacemakers may be characterized as bipolar or unipolar. In bipolar devices, both poles, or terminals, of the pacemaker are connected directly to the distal tip of the lead wires. The ends of the lead wires are tined or have helical screws and are attached directly to the epicardium. This allows the stimulating pulse current from the device to flow through the active tissues between the anode and cathode.

Other bipolar devices feature concentric lead wires that are insulated from each other. These wires terminate at one end in a stimulator connector and at the other end in a pair of metal terminals that are spaced and insulated from each other. The terminals are inserted through a blood vessel into the interior of the heart where the current pulses flowing between the exposed terminals stimulate the epicardial tissues.

The casing of bipolar and unipolar devices is typically sealed in a protective coating to prevent corrosion of the casing and avoid bio-incompatibility problems that might arise from the material of the casing. The coating further serves to electrically insulate the pacemaker from the surrounding tissue. Without proper electrical insulation, the discharges from the device tend to cause unwanted local muscle stimulation, such as pectoral twitching. Thus, U.S. Pat. No. 3,918,460 (King et al.), U.S. Pat. No. 3,924,640 (King), and U.S. Pat. No. 3,943,937 (King et al.) disclose pacemakers and other implantable medical devices, which are entirely encased in an epoxy resin. U.S. Pat. No. 5,220,929 (Marquit) discloses a covering or "boot" for implantable medical devices such as pacemakers. The covering is a bio-compatible material, such as silicone rubber, which seals the device from fluid intrusion. U.S. Pat. No. 4,010,759 (Boer) teaches the use of a tantalum oxide insulating layer to protect a pacemaker from corrosion. Szyszkowski (U.S. Pat. No. 5,282,841) teaches the use of a conductor ribbon to interconnect implantable devices such as pacemakers. The reference notes that the assembly formed from the conductor ribbon and the implantable devices may be encapsulated within a cast epoxy head.

While the above noted devices may be suitable for particular purposes, these devices are bipolar in nature. However, unipolar stimulation is preferable in many cases. In unipolar stimulation, only one of the output terminals from the pacemaker is connected directly to the heart. A second terminal, called an indifferent electrode, is provided as a large area metal plate which is part of the pacemaker casing. Thus, a return conductive path from the heart to the pacemaker is provided by way of the indifferent electrode.

In many known pacemakers, the indifferent electrode is provided as a window in the insulating material of the casing through which the metallic surface of the casing is exposed. Thus, U.S. Pat. No. 3,735,766 (Bowers et al.) discloses a pacemaker that is encapsulated in a resin of medical grade silicone sealant. A tab is embedded in the sealant that may be removed at the time of implantation to expose a portion of the metal surface of the stimulator. Similarly, U.S. Pat. No. 3,971,388 (Cowdery) discloses a pacemaker that is coated with an elastomeric material so that only a selected region of the housing of the pacemaker is exposed to the body. This region is selected to minimize local muscle stimulation.

When pacemakers first came into use, cardiologists prescribing the devices referred their patients to surgeons, who then implanted the devices. By convention, surgeons approach the patient's chest wall from the patient's right side. Therefore, pacemakers have heretofore been designed for right entry. Thus, the terminal connectors on prior art pacemakers are designed to allow insertion of the lead wires from the left-hand side of the device. The pacemakers illustrated in FIG. 1 of U.S. Pat. No. 3,735,766 (Bowers et al.) and FIG. 8 of U.S. Pat. No. 5,282,841 (Szyszkowski) are illustrative.

Recently, however, cardiologists have begun implanting pacemakers without reference to a surgeon. By their own convention, cardiologists approach the patient's chest from the patient's left side. Unfortunately, when the pacemaker is implanted, the lead wires must be twisted or wrapped around the top or head of the pacemaker. This results in a certain amount of torque in the lead wires. This torque is bothersome to the cardiologist during surgery and poses potential problems to the patient, including displacement of the lead wires, fractures or tears of the insulation, electrical parameter changes due to shorts in the line, muscle irritability at the implant site, and tissue erosion. Any of these events can, in turn, cause a host of cardiac problems, including no output from the pacemaker, pulse rate increases or decreases, capture problems, faster cell depletion, or life-threatening infection.

If the pacemaker is inserted through left entry and is not flipped over, other problems arise. Thus, if the device is situated so that the indifferent electrode is facing inward, it will cause twitching in the pectoral muscles each time the device paces in the unipolar mode. If the device is oriented with the terminal connector on the bottom, the lead wire will necessarily be longer to compensate for the increased distance between the terminal connector and the site at which the terminal end of the lead wire is connected to the epicardial tissue. This increase in the length of the lead wire is undesirable because it increases patient trauma associated with replacement of the pacemaker. After a pacemaker is implanted, the patient's tissues grow over the lead wire, necessitating surgical dissection of the lead wire each time the pacemaker is replaced. Thus, the degree of patient trauma associated with replacement of a pacemaker is affected by the length of the lead wire.

There is, thus, a need for a unipolar pacemaker that may be implanted with equal facility on either side of the chest without causing torque in the lead wires and while still avoiding unwanted local muscle stimulation. These and other objects are achieved by the pacemakers of the present invention, as hereinafter disclosed.

SUMMARY OF THE INVENTION

The present invention is a new, improved omnipolar pacemaker, which may be implanted with equal facility on either side of the chest without causing torque in the lead wires and which avoids unwanted local muscle stimulation. In one embodiment, the casing of the pacemaker is provided with a removable tab on each of the opposed sides of the pacemaker. When the device is ready to be implanted, the appropriate tab is removed to expose a portion of the casing on the side facing the patient's chest cavity, thereby allowing for right or left entry into the chest without twisting the lead wires. The exposed portion of the casing serves as the indifferent electrode, so that the device can pace in a unipolar mode.

In a second embodiment, a portion of the edge of the pacemaker is left exposed to serve as the indifferent electrode. This again allows the device to be implanted with equal facility on either side of the chest without causing torque in the lead wires. Furthermore, since the edge of the device is not facing toward the patient's pectoral muscles, the device avoids unwanted pectoral twitching.

In a third embodiment, the terminal connectors are designed to allow insertion of the lead wires from the right side of the device, thereby allowing the pacemaker to be implanted through left entry. Pacemakers of this embodiment may be used to supplement a supply of conventional pacemakers designed for right entry, thereby allowing the surgeon or cardiologist a choice of right or left entry.

DETAILED DESCRIPTION OF THE PREFERRED EMBODIMENT

In accordance with the invention, a programmable polarity pacemaker is provided that may be placed with equal facility on the right or left sides of the chest without causing torsion in the lead wires.

Figure 1:
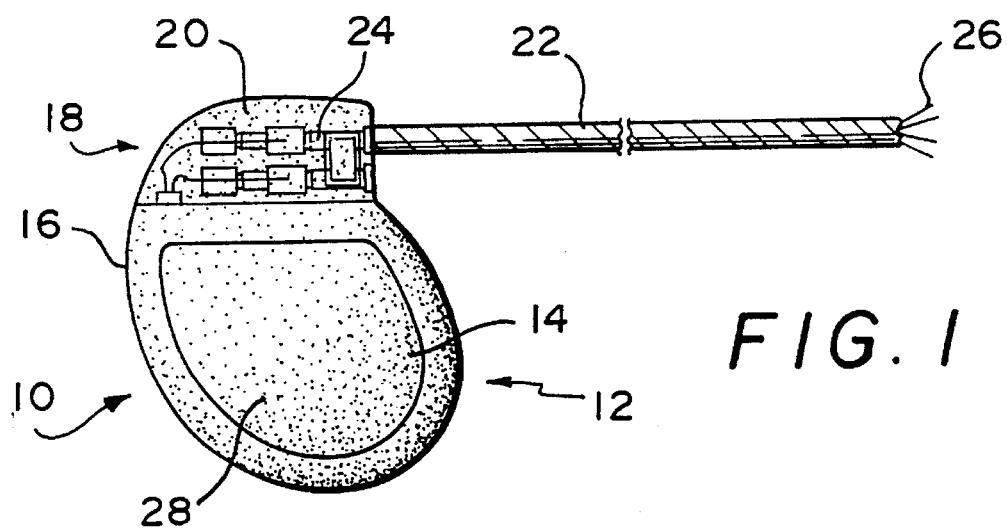
FIG. 1 is a side view of a pacemaker of the present invention showing the tab to be removed when the device is implanted in the right side of the chest to provide for unipolar pacing.
Figure 2:
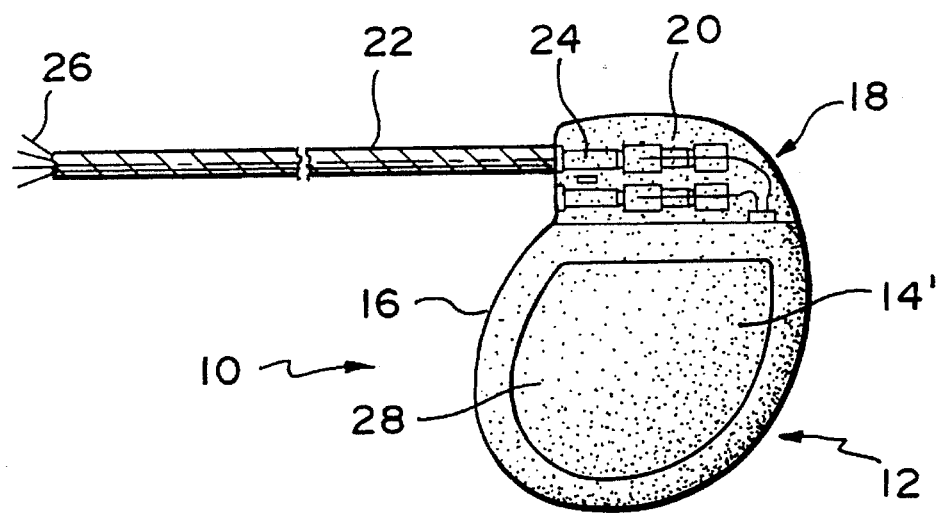
FIG. 2 is a side view of the opposite side of the pacemaker of FIG. 1, showing the tab to be removed when the device is implanted in the left side of the chest to provide for unipolar pacing.

FIGS. 1 and 2 show a first embodiment of a pacemaker 10 in accordance with the invention. The pacemaker comprises a housing 12 having two substantially parallel sides 14, 14' that are joined by an edge 16. The housing encloses the internal circuitry of the pacemaker (not shown), which may include such elements as a pulse generator and a power supply. Suitable circuitry for unipolar pacemakers is well known in the art and is described, for example, in U.S. Pat. No. 3,735,766 (Bowers et al.).

The top of the pacemaker includes a terminal connector 18, which is enclosed in a plastic casing 20 and provides an electrical contact between the lead wires 22 and the internal circuitry of the pacemaker. The connecting end 24 of a lead wire 22 is inserted into the receptacles of the terminal connector, and the terminal end 26 is sutured to the epicardial tissue.

The housing of the pacemaker is preferably constructed of a conductive material, many of which are known in the art. Thus, for example, U.S. Pat. No. 3,971,388 (Cowdery) discloses housings made of titanium and titanium alloys. U.S. Pat. No. 4,010,759 (Boer), in Example 4, describes the use in the prior art of stainless steel casings.

The housing is coated with an electronically insulating, bio-compatible material, many types of which are known in the art. Preferably, the coating is a medical-grade silicone rubber or paralene. Methods for coating pacemakers and other implantable devices with this material are known in the art and are described, for example, in U.S. Pat. No. 3,971,388 (Cowdery) and U.S. Pat. No. 3,735,766 (Bowers et al.).

As noted previously, it is known to provide a pacemaker with a detachable tab that may be removed to expose an indifferent electrode when it is desired to use the pacemaker in a unipolar mode. U.S. Pat. No. 3,735,766 (Bowers et al.) is illustrative, and discusses the construction of both indifferent electrodes and tabs that may be placed over them. However pacemakers have previously been provided with a detachable tab on only one side. In the present invention, by contrast, each side of the housing of the pacemaker is provided with an indifferent electrode plate. A detachable tab 28 is disposed over each electrode plate, thereby allowing the electrode plate to be exposed by removal of the tab.

In use, a physician determines which side of the patient's chest will receive the pacemaker. The physician then removes the tab from the corresponding side of the pacemaker. Thus, for example, if the pacemaker is to be implanted in the right side of the chest, the surgeon will remove the tab from the side depicted in FIG. 1; if, however, the pacemaker is to be implanted in the left side of the patient's chest, the physician will remove the tab depicted in FIG. 2. The pacemaker may then be installed in accordance with normal operating procedures. Since the terminal connector will be properly oriented in the direction of the lead wires, there will be no need to twist the lead wires around the terminal connector when the pacemaker is implanted.

Figure 3:
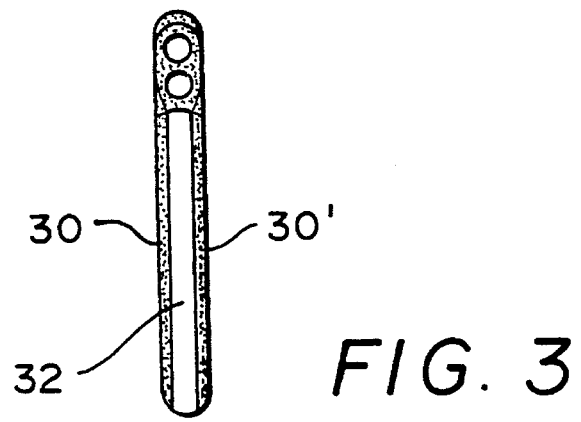
FIG. 3 is a view of the edge of a second embodiment of a pacemaker of the present invention showing an edge that is left uncoated to serve as the indifferent electrode.

FIG. 3 illustrates a second embodiment of the present invention. In this embodiment, the housing of the pacemaker is coated with an electrically insulating material on each side 30', but the edge 32 of the housing is left uncoated to serve as the indifferent electrode. This allows the pacemaker to be placed with equal facility on either side of the patient's chest, without causing torque in the lead wires. Furthermore, since the side of the pacemaker facing the patient's pectoral muscles is coated with an electrically insulating material, local muscle stimulation, such as pectoral twitching, does not occur.

A third embodiment of the present invention is also possible. In this embodiment, most of the housing of the pacemaker is coated with an electrically insulating material, but a portion of the housing on one side is left uncoated to serve as the indifferent electrode. The device differs from similar prior art pacemakers in that the terminal connector is designed to allow insertion of the lead wires from the right hand side of the device, thereby allowing the pacemaker to be implanted through left entry into the chest cavity. This may be accomplished, for example, by constructing the terminal connector so that it is directed toward the right hand side of the device when the device is properly oriented within the chest cavity. Pacemakers of this embodiment may be used to supplement a supply of conventional pacemakers designed for right entry, thereby allowing the surgeon or cardiologist a choice of right or left entry.

The above disclosure is intended only to convey an understanding of the present invention to those skilled in the art, and is not intended to be limiting. It will be appreciated that various modifications to the disclosed embodiments are possible without departing from the scope of the invention. Therefore, the scope of the present invention should be construed solely by reference to the appended claims.

What is claimed is:

1. A pacemaker, comprising:

a housing comprising a first side of electrically conductive material and a second side of electrically conductive material;

an electrically insulating coating covering said housing;

first exposing means in said electrically insulating material for selectively exposing a portion of the surface of said first side; and second exposing means in said electrically insulating material for selectively exposing a portion of the surface of said second side.

2. The pacemaker of claim 1, wherein said coating is bio-compatible.

3. The pacemaker of claim 1, wherein said first exposing means and said second exposing means comprise tabs that remove a portion of said coating, thereby exposing a portion of said housing.

4. The pacemaker of claim 3, wherein the portion of said housing so exposed is an indifferent electrode.

5. A housing for a programmable polarity pacemaker, comprising:

a first side comprising an electrically conductive material;

a second side comprising an electrically conductive material;

an edge joining said first and second sides, said edge comprising an electrically conductive surface, and electrical insulating means for coating said first and second sides with a non-conductive material and for exposing said edge.

6. The pacemaker of claim 5, wherein said first side and said second side are flat.

7. The pacemaker of claim 6, wherein said first side and said second side are parallel.

8. A pacemaker, comprising:

electrically conductive housing means for housing a pulse generator;

insulating means disposed on said housing means, for electrically insulating the external surface of said housing means;

first exposing means for exposing selectively a first portion of the external surface of said housing means; and second exposing means for exposing selectively a second portion of the external surface of said housing means.

9. The pacemaker of claim 8, wherein said housing means comprises a first side, a second side, and an edge portion joining said first and second sides.

10. The pacemaker of claim 9, wherein said first exposing means is disposed on said first side.

11. The pacemaker of claim 10, wherein said second exposing means is disposed on said second side.

12. The pacemaker of claim 8, wherein said first exposing means and said second exposing means comprise removable tabs.

* * * * *